US011439443B2

United States Patent
Min et al.

(10) Patent No.: US 11,439,443 B2
(45) Date of Patent: Sep. 13, 2022

(54) ROD REDUCING DEVICE

(71) Applicant: K2M, Inc., Leesburg, VA (US)

(72) Inventors: Kan Min, Rüschlikon (CH); Brian Kunes, Arlington, VA (US)

(73) Assignee: K2M, Inc., Leesburg, VA (US)

(*) Notice: Subject to any disclaimer, the term of this patent is extended or adjusted under 35 U.S.C. 154(b) by 403 days.

(21) Appl. No.: 16/655,421

(22) Filed: Oct. 17, 2019

(65) Prior Publication Data
US 2020/0046410 A1 Feb. 13, 2020

Related U.S. Application Data

(63) Continuation of application No. 15/873,370, filed on Jan. 17, 2018, now Pat. No. 10,485,590.

(60) Provisional application No. 62/447,519, filed on Jan. 18, 2017.

(51) Int. Cl.
*A61B 17/88* (2006.01)
*A61B 17/70* (2006.01)

(52) U.S. Cl.
CPC ...... *A61B 17/7086* (2013.01); *A61B 17/7002* (2013.01); *A61B 17/7091* (2013.01); *A61B 17/7032* (2013.01); *A61B 17/7041* (2013.01); *A61B 17/7085* (2013.01)

(58) Field of Classification Search
CPC ............ A61B 17/7086; A61B 17/7002; A61B 17/7091; A61B 17/7032; A61B 17/7041; A61B 17/7085
USPC ................................ 606/265, 279, 99, 86 A
See application file for complete search history.

(56) References Cited

U.S. PATENT DOCUMENTS

| | | | |
|---|---|---|---|
| 2,248,054 | A | 7/1941 | Becker |
| 3,604,487 | A | 9/1971 | Gilbert |
| 4,263,899 | A | 4/1981 | Burgin |
| 5,020,519 | A | 6/1991 | Hayes et al. |

(Continued)

FOREIGN PATENT DOCUMENTS

| | | |
|---|---|---|
| FR | 2985166 A1 | 7/2013 |
| JP | 2008508935 A | 3/2008 |
| WO | 2016175885 A1 | 11/2016 |

OTHER PUBLICATIONS

Extended European Search Report including Written Opinion for EP3351195 dated Jun. 15, 2018.

*Primary Examiner* — Eduardo C Robert
*Assistant Examiner* — David C Comstock
(74) *Attorney, Agent, or Firm* — Lerner, David, Littenberg, Krumholz & Mentlik, LLP

(57) ABSTRACT

A rod reducer includes a housing, an anvil, a locking anvil configured to engage a locking plug of a bone screw assembly, an arm assembly, a reducing screw extending through the housing and rotatably coupled with the anvil, and a locking screw extending through the housing and rotatably coupled with the locking anvil. The arm assembly includes an arm hingedly coupled to the housing, and first and second grasping members configured to engage the bone screw assembly. The first and second grasping members are hingedly coupled to the housing and extend through the anvil. Rotation of the reducing screw transitions the arm assembly between an open position, in which, distal portions of the arm and the first and second grasping members are radially expanded, and a closed position, in which, the distal portions of the arm and the first and second grasping members are radially contracted.

18 Claims, 13 Drawing Sheets

(56) References Cited

U.S. PATENT DOCUMENTS

| | | |
|---|---|---|
| 5,364,397 A | 11/1994 | Hayes et al. |
| 5,420,751 A | 5/1995 | Burns |
| 5,431,658 A | 7/1995 | Moskovich |
| 5,466,243 A | 11/1995 | Schmieding et al. |
| 5,529,571 A | 6/1996 | Daniel |
| 5,685,826 A | 11/1997 | Bonutti |
| 5,720,751 A | 2/1998 | Jackson |
| 5,910,141 A | 6/1999 | Morrison et al. |
| 5,944,658 A | 8/1999 | Koros et al. |
| 5,951,564 A | 9/1999 | Schroder et al. |
| 6,123,707 A | 9/2000 | Wagner |
| 6,200,322 B1 | 3/2001 | Branch et al. |
| 6,416,521 B1 | 7/2002 | Waldner et al. |
| 6,440,133 B1 | 8/2002 | Beale et al. |
| 6,488,682 B2 | 12/2002 | Kikuchi et al. |
| 6,616,605 B2 | 9/2003 | Wright et al. |
| 6,648,888 B1 | 11/2003 | Shluzas |
| 6,660,006 B2 | 12/2003 | Markworth et al. |
| 6,743,231 B1 | 6/2004 | Gray et al. |
| 6,746,449 B2 | 6/2004 | Jones et al. |
| 6,790,208 B2 | 9/2004 | Oribe et al. |
| 6,790,209 B2 | 9/2004 | Beale et al. |
| 6,849,064 B2 | 2/2005 | Hamada |
| 6,875,211 B2 | 4/2005 | Nichols et al. |
| 6,923,814 B1 | 8/2005 | Hildebrand et al. |
| 6,929,606 B2 | 8/2005 | Ritland |
| 6,932,822 B2 | 8/2005 | Oribe et al. |
| 6,957,758 B2 | 10/2005 | Aranyi |
| 7,008,422 B2 | 3/2006 | Foley et al. |
| 7,011,660 B2 | 3/2006 | Sherman et al. |
| 7,083,621 B2 | 8/2006 | Shaolian et al. |
| 7,156,849 B2 | 1/2007 | Dunbar et al. |
| 7,160,300 B2 | 1/2007 | Jackson |
| 7,179,261 B2 | 2/2007 | Sicvol et al. |
| 7,188,626 B2 | 3/2007 | Foley et al. |
| 7,226,453 B2 | 6/2007 | Chao et al. |
| 7,250,052 B2 | 7/2007 | Landry et al. |
| 7,371,239 B2 | 5/2008 | Dec et al. |
| 7,462,182 B2 | 12/2008 | Lim |
| 7,473,267 B2 | 1/2009 | Nguyen et al. |
| 7,481,813 B1 | 1/2009 | Purcell |
| 7,491,207 B2 | 2/2009 | Keyer et al. |
| 7,491,208 B2 | 2/2009 | Pond, Jr. et al. |
| 7,497,869 B2 | 3/2009 | Justis |
| 7,520,879 B2 | 4/2009 | Justis et al. |
| 7,547,318 B2 | 6/2009 | Birkmeyer et al. |
| 7,563,264 B2 | 7/2009 | Landry et al. |
| 7,572,264 B2 | 8/2009 | Null et al. |
| 7,572,281 B2 | 8/2009 | Runco et al. |
| 7,575,581 B2 | 8/2009 | Lovell |
| 7,588,575 B2 | 9/2009 | Colleran et al. |
| 7,588,588 B2 | 9/2009 | Spitler et al. |
| 7,591,836 B2 | 9/2009 | Dick et al. |
| 7,608,081 B2 | 10/2009 | Abdelgany |
| 7,611,517 B2 | 11/2009 | Lim |
| 7,618,442 B2 | 11/2009 | Spitler et al. |
| 7,621,918 B2 | 11/2009 | Jackson |
| 7,625,379 B2 | 12/2009 | Puno et al. |
| 7,637,914 B2 | 12/2009 | Stern |
| 7,651,502 B2 | 1/2010 | Jackson |
| 7,655,008 B2 | 2/2010 | Lenke et al. |
| 7,666,189 B2 | 2/2010 | Gerber et al. |
| 7,691,132 B2 | 4/2010 | Landry et al. |
| 7,708,763 B2 | 5/2010 | Selover et al. |
| 7,776,040 B2 | 8/2010 | Markworth et al. |
| 7,824,413 B2 | 11/2010 | Varieur et al. |
| 7,854,751 B2 | 12/2010 | Sicvol et al. |
| 7,887,539 B2 | 2/2011 | Dunbar, Jr. et al. |
| 7,887,541 B2 | 2/2011 | Runco et al. |
| 7,909,835 B2 | 3/2011 | Oribe et al. |
| 7,922,749 B2 | 4/2011 | Dewey |
| 7,927,334 B2 | 4/2011 | Miller et al. |
| 7,946,982 B2 | 5/2011 | Hamada |
| 7,955,355 B2 | 6/2011 | Chin |
| 7,988,694 B2 | 8/2011 | Barrus et al. |
| 8,002,798 B2 | 8/2011 | Chin et al. |
| 8,147,524 B2 | 4/2012 | Piza Vallespir |
| 8,152,810 B2 | 4/2012 | Jackson |
| 8,162,991 B2 | 4/2012 | Strauss et al. |
| 8,192,438 B2 | 6/2012 | Garamszegi |
| 8,230,863 B2 | 7/2012 | Ravikumar et al. |
| 8,298,138 B2 | 10/2012 | Gorek et al. |
| 8,303,595 B2 | 11/2012 | Jones |
| 8,308,729 B2 | 11/2012 | Nunley et al. |
| 8,308,774 B2 | 11/2012 | Hoffman et al. |
| 8,956,360 B2 | 2/2015 | Boachie-Adjei et al. |
| 8,961,523 B2 | 2/2015 | Barrus et al. |
| 9,198,698 B1 | 12/2015 | Doose et al. |
| 9,247,969 B2 * | 2/2016 | Nunley .............. A61B 17/7086 |
| 9,452,000 B2 | 9/2016 | Barrus |
| 9,532,816 B2 | 1/2017 | Barrus et al. |
| 9,655,664 B2 | 5/2017 | Barrus et al. |
| 2002/0052603 A1 | 5/2002 | Nichols et al. |
| 2003/0009168 A1 | 1/2003 | Beale et al. |
| 2003/0225408 A1 | 12/2003 | Nichols et al. |
| 2004/0147937 A1 | 7/2004 | Dunbar et al. |
| 2004/0215190 A1 | 10/2004 | Nguyen et al. |
| 2004/0230191 A1 | 11/2004 | Frey et al. |
| 2004/0267275 A1 | 12/2004 | Cournoyer et al. |
| 2005/0059969 A1 | 3/2005 | McKinley |
| 2005/0096653 A1 | 5/2005 | Doubler et al. |
| 2005/0143749 A1 | 6/2005 | Zalenski et al. |
| 2005/0149053 A1 | 7/2005 | Varieur et al. |
| 2005/0192570 A1 | 9/2005 | Jackson |
| 2005/0192579 A1 | 9/2005 | Jackson |
| 2005/0192587 A1 | 9/2005 | Lim |
| 2005/0192589 A1 | 9/2005 | Raymond et al. |
| 2005/0261702 A1 | 11/2005 | Oribe et al. |
| 2005/0277934 A1 | 12/2005 | Vardiman |
| 2006/0009775 A1 | 1/2006 | Dec et al. |
| 2006/0025769 A1 | 2/2006 | Dick et al. |
| 2006/0036254 A1 | 2/2006 | Lim |
| 2006/0036255 A1 | 2/2006 | Pond et al. |
| 2006/0036260 A1 | 2/2006 | Runco et al. |
| 2006/0074418 A1 | 4/2006 | Jackson |
| 2006/0079909 A1 | 4/2006 | Runco et al. |
| 2006/0089651 A1 | 4/2006 | Trudeau et al. |
| 2006/0200132 A1 | 9/2006 | Chao et al. |
| 2006/0247630 A1 | 11/2006 | Iott et al. |
| 2006/0271050 A1 | 11/2006 | Piza Vallespir |
| 2006/0293692 A1 | 12/2006 | Whipple et al. |
| 2007/0016193 A1 | 1/2007 | Ritland |
| 2007/0055247 A1 | 3/2007 | Jahng |
| 2007/0093817 A1 | 4/2007 | Barrus et al. |
| 2007/0213716 A1 | 9/2007 | Lenke et al. |
| 2007/0213722 A1 | 9/2007 | Jones et al. |
| 2007/0260261 A1 | 11/2007 | Runco et al. |
| 2007/0270811 A1 | 11/2007 | Dewey |
| 2007/0270867 A1 | 11/2007 | Miller et al. |
| 2007/0276379 A1 | 11/2007 | Miller et al. |
| 2007/0282337 A1 | 12/2007 | Garamszegi |
| 2008/0015601 A1 | 1/2008 | Castro et al. |
| 2008/0045955 A1 | 2/2008 | Berrevoets et al. |
| 2008/0172062 A1 | 7/2008 | Donahue et al. |
| 2009/0018593 A1 | 1/2009 | Barrus et al. |
| 2009/0143828 A1 | 6/2009 | Stad et al. |
| 2009/0228053 A1 | 9/2009 | Kolb et al. |
| 2010/0121385 A1 | 5/2010 | Blain et al. |
| 2011/0054259 A1 | 3/2011 | Gorek et al. |
| 2011/0118791 A1 | 5/2011 | Nunley et al. |
| 2011/0172714 A1 | 7/2011 | Boachie-Adjei et al. |
| 2011/0172723 A1 | 7/2011 | Miller et al. |
| 2011/0257692 A1 | 10/2011 | Sandstrom et al. |
| 2012/0083853 A1 | 4/2012 | Boachie-Adjei et al. |
| 2012/0191144 A1 | 7/2012 | Peultier et al. |
| 2012/0271365 A1 | 10/2012 | Daubs et al. |
| 2012/0277808 A1 | 11/2012 | May |
| 2013/0041228 A1 | 2/2013 | Gorek et al. |
| 2013/0046344 A1 | 2/2013 | Nunley et al. |
| 2013/0245702 A1 | 9/2013 | McBride |
| 2014/0058464 A1 | 2/2014 | Hutchens |
| 2014/0163617 A1 | 6/2014 | Boachie-Adjei et al. |
| 2014/0163625 A1 | 6/2014 | Meyer et al. |
| 2014/0277170 A1 | 9/2014 | Barrett et al. |

(56) References Cited

U.S. PATENT DOCUMENTS

| | | | |
|---|---|---|---|
| 2014/0364912 A1* | 12/2014 | May | A61B 17/7043 |
| | | | 606/253 |
| 2015/0066042 A1 | 3/2015 | Cummins et al. | |
| 2015/0100097 A1 | 4/2015 | Barrus | |
| 2015/0100098 A1 | 4/2015 | Moore | |
| 2015/0173809 A1 | 6/2015 | Bechtel et al. | |
| 2015/0272628 A1 | 10/2015 | Kishan et al. | |
| 2016/0206354 A1 | 7/2016 | Mladenov et al. | |
| 2016/0346011 A1 | 12/2016 | Angus | |
| 2020/0397486 A1* | 12/2020 | Mladenov | A61B 17/7002 |
| 2021/0145489 A1* | 5/2021 | Barrus | A61B 17/7086 |

\* cited by examiner

ROD REDUCING DEVICE

CROSS-REFERENCE TO RELATED APPLICATIONS

This application is a continuation of U.S. application Ser. No. 15/873,370, filed on Jan. 17, 2018 which claims the benefit of U.S. Provisional Application Ser. No. 62/447,519, which was filed on Jan. 18, 2017, the entire contents of which are incorporated herein by reference.

TECHNICAL FIELD

The present disclosure relates to spinal surgery and, more particularly, to systems, devices, and methods for reducing spinal rods into bone screw housings and/or for manipulation of a spinal column.

BACKGROUND

There are various disorders, diseases and types of injury, which the spinal column may experience in a lifetime. One of the more common solutions to treating these conditions involves a surgical procedure utilizing mechanical hardware. The mechanical hardware used to immobilize the spinal column typically involves a series of bone screws and spinal rods or plates. When the spine surgery is performed, it is common practice to place bone screws into the vertebral bodies and then connect a spinal rod between adjacent vertebral bodies.

The process of properly inserting the spinal rod into the receiving slot of a bone screw and then securing that connecting spinal rod in place often can require that the surgeon use a number of instruments and expend a great deal of time and effort to accomplish the task. When bone screws in several adjacent vertebrae are to be securely connected by a spinal rod, the repeated process of inserting the spinal rod into the heads of the bone screws and then securing the spinal rod in place for each respective bone screw can be difficult, tiresome and time consuming. Further, the alignment of the spinal rod as it connects to each of the sequential bone screws may require adjustment during the procedure and, therefore it is beneficial that a device and method be provided by which the spinal rod can be reduced into the head of each of the sequentially aligned bone screws and, as desired, easily adjusted so as to facilitate the process for the surgeon with minimal effort and loss of time.

For these reasons there remains a need for a device that is capable of securely grasping the head of a bone screw in a controlled, measured manner and reducing a spinal rod into the head of that bone screw in such a way as to permit easy position adjustment as other portions of the spinal rod are reduced into other bone screws.

SUMMARY

In accordance with an embodiment of the present disclosure, there is provided a rod reducer that effectively reduces in a controlled, measured way a spinal rod into position in a head of a bone screw and holds that spinal rod in position while other portions of the spinal rod are positioned and reduced into other bone screws allowing for position adjustment as necessary during the process. The rod reducer includes a housing, an anvil, a locking anvil, an arm assembly, a reducing screw, and a locking screw. The anvil is operatively coupled with the housing, and includes a rod positioning portion configured to engage a spinal rod. The locking anvil is configured to engage a locking plug of a bone screw assembly. The arm assembly includes an arm hingedly coupled to the housing and extending through the anvil, and first and second grasping members configured to engage the bone screw assembly. The first and second grasping members are hingedly coupled to the housing and extend through the anvil. The reducing screw extends through the housing and is rotatably coupled with the anvil. The locking screw extends through the housing and is rotatably coupled with the locking anvil. Rotation of the reducing screw transitions the arm assembly between an open position, in which, distal portions of the arm and the first and second grasping members are radially expanded, and a closed position, in which, the distal portions of the arm and the first and second grasping members are radially contracted.

In an embodiment, the reducing screw may be rotatably coupled with the anvil while inhibiting relative axial displacement therebetween.

In another embodiment, the housing may define a plurality of cutouts dimensioned to receive the arm and the first and second grasping members.

In yet another embodiment, the anvil may include an elongate member defining a threaded bore configured to threadably engage the locking screw.

In still yet another embodiment, the locking screw may be rotatably coupled with the locking anvil while inhibiting relative axial displacement therebetween.

In another embodiment, the first and second grasping members may define first and second guide channels dimensioned to engage the bone screw assembly when the arm assembly is in the closed position.

In yet another embodiment, the rod positioning portion of the anvil may define an arcuate recess configured to engage the spinal rod.

In still yet another embodiment, the reducing screw may threadably engage the housing.

In an embodiment, the anvil may define a cutout configured to slidably receive at least a portion of the locking anvil to facilitate axial displacement of the locking anvil relative to the anvil.

In accordance with another embodiment of the present disclosure, there is provided a system for reducing a spinal rod into a bone screw assembly including a spinal rod, a bone screw assembly, and a rod reducer. The bone screw assembly includes a rod receiving portion configured to receive the spinal rod, and a housing including a locking plug transitionable between a locked state, in which, the spinal rod is securely fixed to the rod receiving portion and an unlocked state, in which, the spinal rod is repositionable with respect to the rod receiving portion. The rod reducer includes a housing, an anvil operatively coupled with the housing, a locking anvil configured to engage the locking plug of the bone screw assembly, an arm assembly, a reducing screw, and a locking screw. The anvil includes a rod positioning portion configured to engage the spinal rod. The arm assembly includes an arm hingedly coupled to the housing and extending through the anvil, and a pair of grasping members configured to engage the bone screw assembly. The pair of grasping members is hingedly coupled to the housing and extends through the anvil. The reducing screw extends through the housing and is rotatably coupled with the anvil. The locking screw extends through the housing and is rotatably coupled with the locking anvil. Rotation of the reducing screw transitions the arm assembly between an open position, in which, distal portions of the arm and the pair of grasping members are radially expanded, and a closed position, in which, the distal portions of the arm and the pair of grasping members are radially contracted.

In an embodiment, rotation of the locking screw may cause axial displacement of the locking anvil relative to the anvil.

In another embodiment, the arm may be configured to engage the rod receiving portion of the bone screw when the arm assembly is in the closed position.

In yet another embodiment, the locking anvil may be configured to impart axial force to the locking plug of the bone screw assembly to transition the housing of the bone screw assembly between the unlocked state to the locked state.

In accordance with another aspect of the present disclosure, there is provided a method of reducing a spinal rod including transitioning a rod reducer to an open state, in which, distal ends of an arm and grasping members of the rod reducer are radially expanded; mounting the rod reducer over a bone screw assembly; positioning a spinal rod adjacent a rod receiving portion of the bone screw assembly; rotating a reducing screw of the rod reducer to transition an anvil of the rod reducer away from a housing of the rod reducer to a closed state, in which, the distal ends of the arm and the grasping members of the rod reducers are radially contracted to engage the bone screw assembly; reducing the spinal rod into the rod receiving portion; and securing the spinal rod to the rod receiving portion by rotating a locking screw of the rod reducer to advance a locking plug into a bone screw housing of the bone screw assembly.

In an embodiment, rotating the reducing screw of the rod reducer may include engaging the arm of the rod reducer with the rod receiving portion of the bone screw.

In another embodiment, rotating the reducing screw of the rod reducer may include engaging the grasping members with the bone screw housing of the bone screw assembly.

In yet another embodiment, partially inserting the locking plug into the bone screw housing of the bone screw assembly may include making adjustments to the spinal rod.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
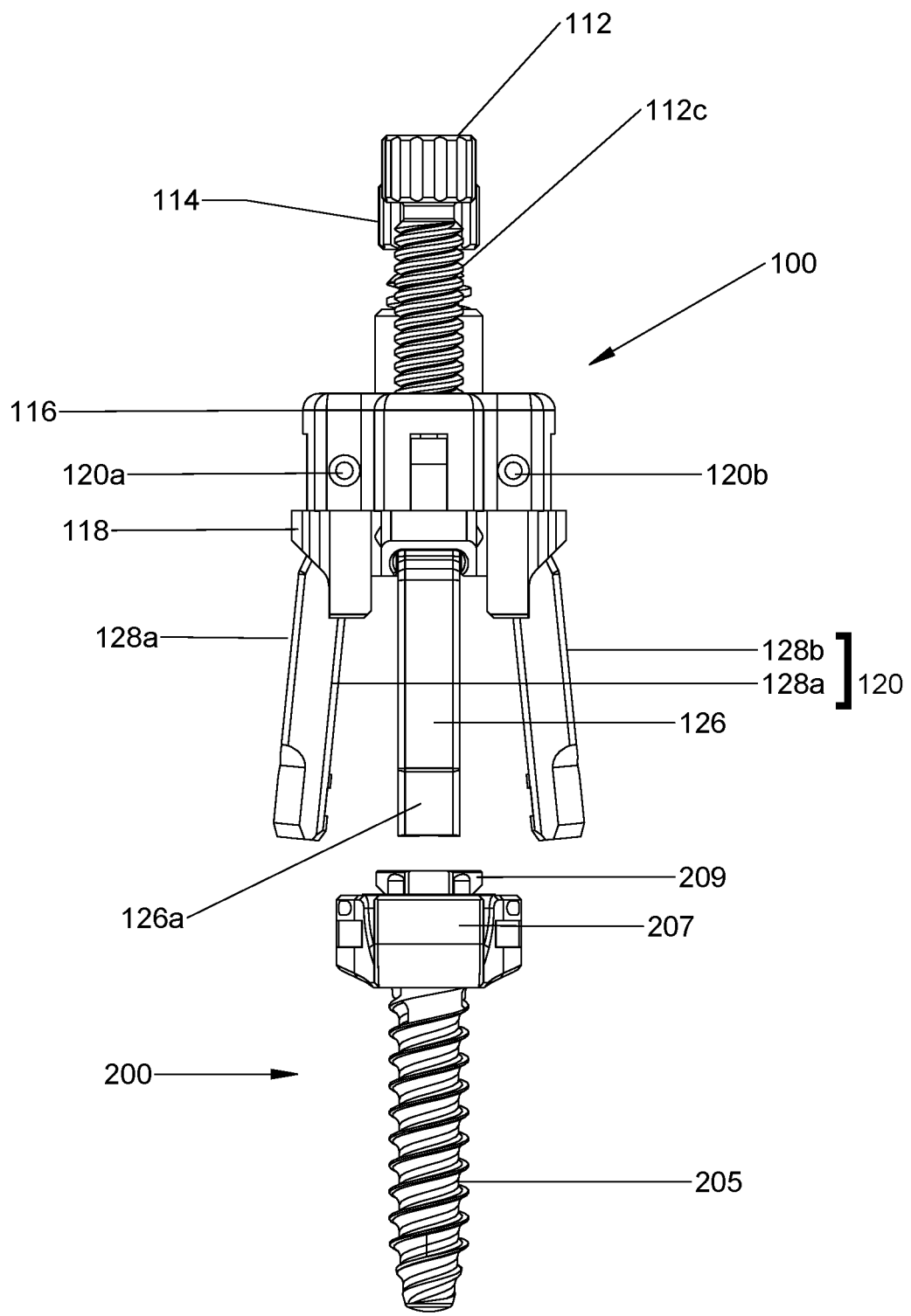
FIG. 1 is a front view of a rod reducer and a bone screw assembly in accordance with an embodiment of the present disclosure.

Embodiments of the presently disclosed devices are described in detail with reference to the drawings, in which like reference numerals designate identical or corresponding elements in each of the several views. As used herein, the term "distal" or "leading" refers to that portion of the device that is farther from the user, while the term "proximal" or "trailing" refers to that portion of the device that is closer to the user. In addition, the term "cephalad" is known to indicate a direction toward a patient's head, whereas the term "caudad" indicates a direction toward the patient's feet. Further still, the term "lateral" is understood to indicate a direction toward a side of the body of the patient, i.e., away from the middle of the body of the patient. The term "posterior" indicates a direction toward the patient's back, and the term "anterior" indicates a direction toward the patient's front. As used herein, the term "clinician" refers to a doctor, nurse, or other care provider and may include support personnel. In the following description, well-known functions or constructions are not described in detail to avoid obscuring the present disclosure in unnecessary detail.

Figure 2:
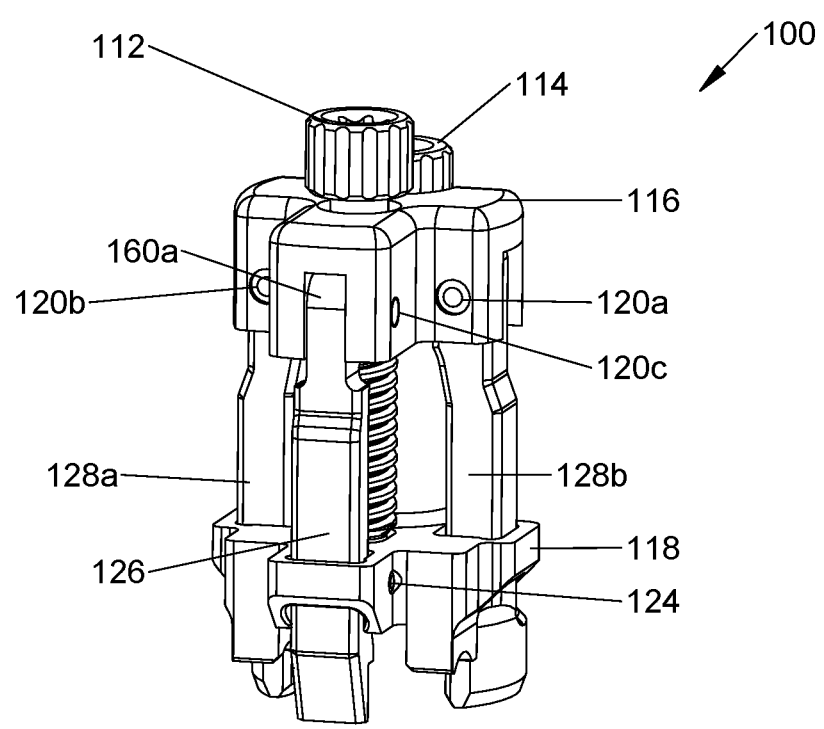
FIG. 2 is a perspective view of the rod reducer of FIG. 1.
Figure 3:
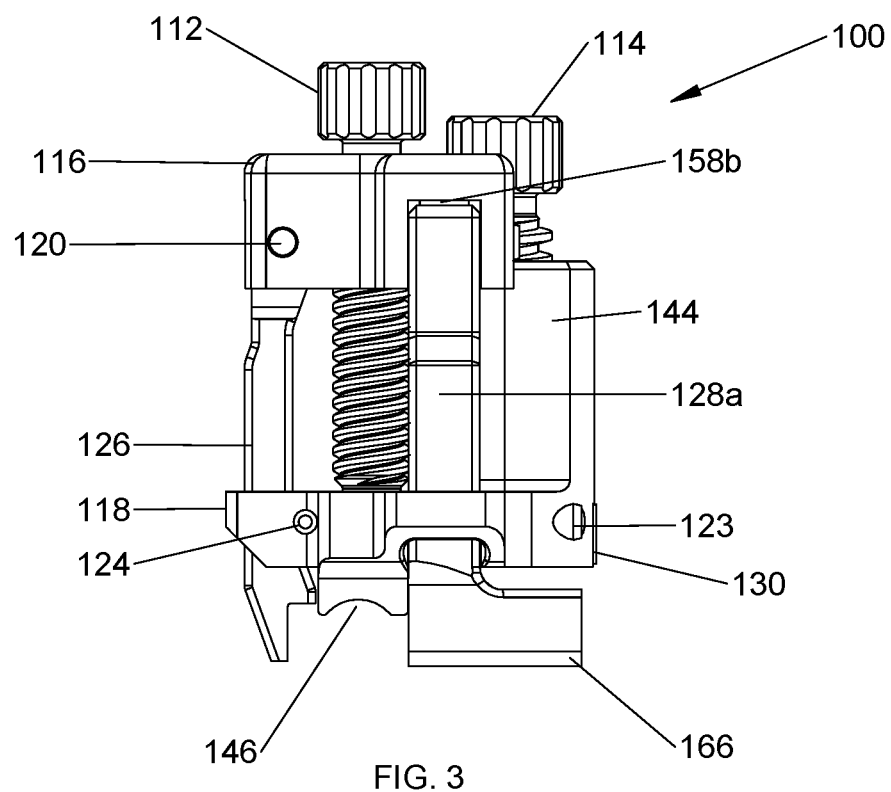
FIG. 3 is a side view of the rod reducer of FIG. 2.
Figure 4:
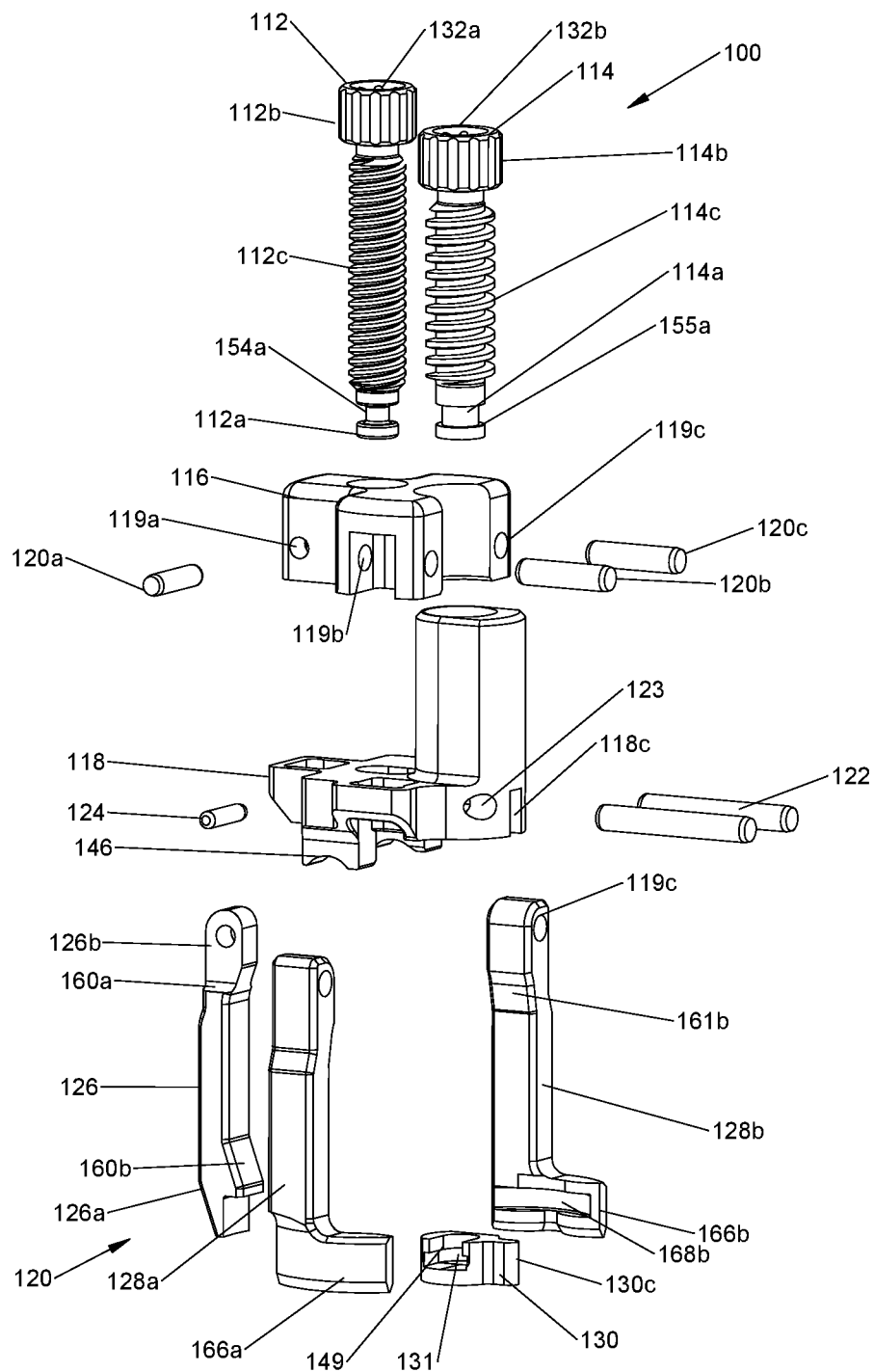
FIG. 4 is an exploded perspective view of the rod reducer of FIG. 1 with parts separated.

With reference to FIGS. 1-3, a system for reducing a spinal rod is shown and generally designated as 10. The system 10 for reducing a spinal rod 300 (FIG. 14) includes a rod reducer 100, a bone screw assembly 200, and the spinal rod 300. The rod reducer 100 is configured to be mounted on the bone screw assembly 200 to reduce the spinal rod 300 into a bone screw housing 207 of the bone screw assembly 200. The rod reducer 100 includes a housing 116, an anvil 118 configured to engage the spinal rod 300 to place the spinal rod 300 in the bone screw housing 207, an arm assembly 120 operatively coupled with the housing 116, a locking anvil 130 (FIG. 4) configured to engage a locking plug 209 of the bone screw assembly 200 in order to securely fix the spinal rod 300 with the bone screw assembly 200, a reducing screw 112 operatively coupled with the anvil 118, and a locking screw 114 operatively coupled with the locking anvil 130 (FIG. 4). The housing 116 and the anvil 118 may be unitary structures.

Figure 5:
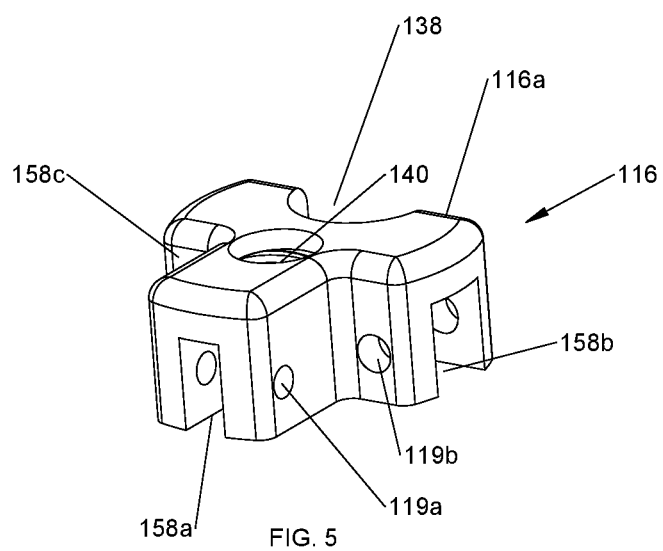
FIG. 5 is a perspective view of a housing of the rod reducer of FIG. 1.

With reference to FIGS. 4 and 5, the housing 116 includes a body 116a defining a bore 140 configured to threadably receive the reducing screw 112 therein, and a recess 138 dimensioned to receive the locking screw 114 therein. The housing 116 includes cutout portions 158a, 158b, 158c. The cutout portion 158a defines opposing holes 119a dimensioned to receive a pin 120a to hingedly secure an arm 126 of the arm assembly 120 (FIG. 1) to the housing 116. Similarly, the cutout portions 158b, 158c define respective holes 119b, 119c dimensioned to receive respective pins 120b, 120c to hingedly secure respective grasping members 128a, 128b of the arm assembly 120 to the housing 116. The cutout portions 158b, 158c may oppose each other such that the grasping members 128a, 128b may engage diametrically opposed portions of the bone screw housing 207 (FIG. 1) of the bone screw assembly 200 for secure and balanced engagement with the bone screw assembly 200. The bore 140 may be centrally defined in the body 116a, and the recess 138 may be interposed between the cutout portions 158b, 158c. In addition, the recess 138 may include an arcuate profile to receive the locking screw 114.

With particular reference to FIG. 4, the reducing screw 112 includes a distal portion 112a defining an annular groove 154a configured to rotatably engage a tongue portion 148a (FIG. 6) of a third hole 140b defined in a base portion 118a of the anvil 118, a proximal portion 112b defining a cavity 132a, and a threaded portion 112c extending between the proximal and distal portions 112a, 112b. The cavity 132a includes, e.g., a hex, key feature for non-slip engagement with a driver or other instrument (not shown) to drive the reducing screw 112. Similarly, the locking screw 114 includes a distal portion 114a defining an annular groove 155a configured to rotatably engage a tongue portion 149 of the locking anvil 130, a proximal portion 114b defining a cavity 132b, and a threaded portion 114c extending between the proximal and distal portions 114a, 114b. The cavity 132b includes, e.g., a hex, key feature for non-slip engagement with a driver or other instrument (not shown) to drive the locking screw 112. It is contemplated that cavities 132a, 132b may have any suitable configuration such as, e.g., slotted, square, star fitting, or a Phillips head, for engagement with the driver. It is also envisioned that the threaded portions 114c of the locking screw 114 may be, e.g., a coarse acme thread, configured to support more load, whereas the threaded portion 112c on the reducing screw 112 may be a finer thread.

Figure 6:
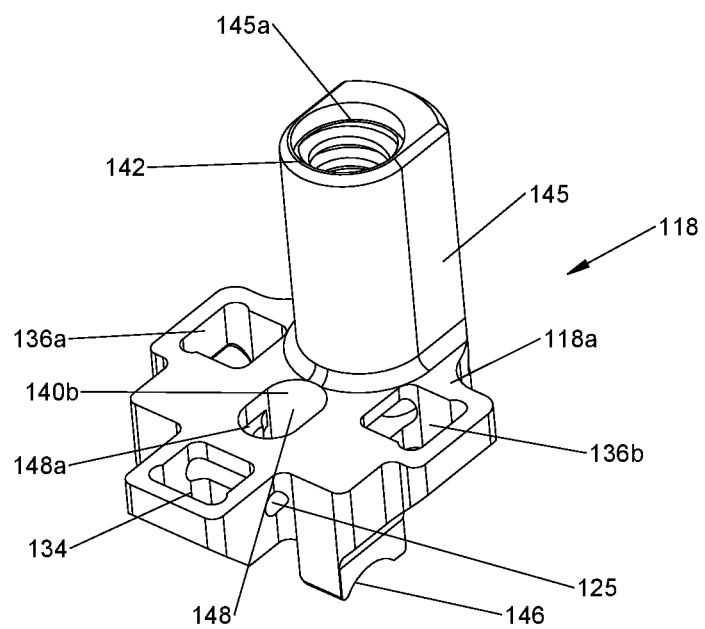
FIG. 6 is a perspective view of an anvil of the rod reducer of FIG. 1.
Figure 7:
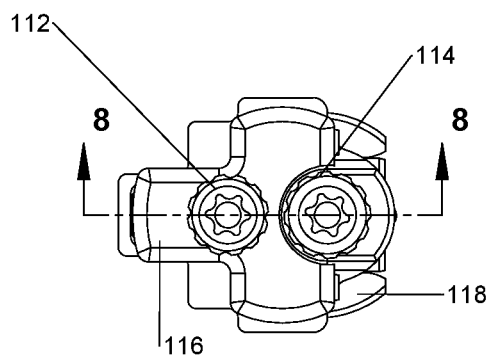
FIG. 7 is a top view of the rod reducer of FIG. 2.

With reference now to FIGS. 4 and 6, the anvil 118 includes a base portion 118a, an elongate portion 145 extending proximally from the base portion 118a, and a pair of rod positioning portions or rod positioning members 146 (only one shown) extending distally from the base portion 118a. The base portion 118a defines a hole 134 dimensioned to receive the arm 126 therethrough, second holes 136a, 136b dimensioned to receive the respective grasping members 128a, 128b therethrough, and a third hole 140b dimensioned to receive the reducing screw 112. In particular, an inner wall 148 of the third hole 140b includes a tongue portion 148a extending radially inward from the inner wall 148. The tongue portion 148a is configured to engage the annular groove 154a of the reducing screw 112 such that the reducing screw 112 is rotatably secured with the anvil 118, while inhibiting relative axial movement with the anvil 118. The elongate portion 145 extends proximally from the base portion 118a. The elongate portion 145 defines a threaded bore 145a configured to threadably engage the locking screw 114. The rod positioning members 146 extend distally from the base portion 118a and are configured to engage the spinal rod 300 (FIG. 14) to position the spinal rod 300 into the bone screw housing 207 (FIG. 1) of the bone screw assembly 200.

The base portion 118a further defines a locking pin hole 123 (FIG. 4) dimensioned to receive a locking pin 122. The locking pin 122 is configured to limit axial displacement of the locking screw 114. The base portion 118a can further define a cam pin hole 125 that extends across a portion of the hole 134. The cam pin hole 125 can be configured and dimensioned to receive a cam pin 124 (FIG. 4). Under such a configuration, when the rod reducer 100 transitions between open (FIG. 9) and closed positions (FIG. 2), i.e., radial expansion and contraction of the arm 126 and the grasping members 128a, 128b, camming portions 160a, 160b of the arm 126 can slidably engage the cam pin 124. In the open position (FIG. 9), each of the arm 126 and the grasping members 128a, 128b defines an acute angle with respect to a central longitudinal axis of the housing 116. In the closed position (FIG. 2), each of the arm 126 and the grasping members 128a, 128b is substantially parallel with the central longitudinal axis of the housing 116.

Figure 8:
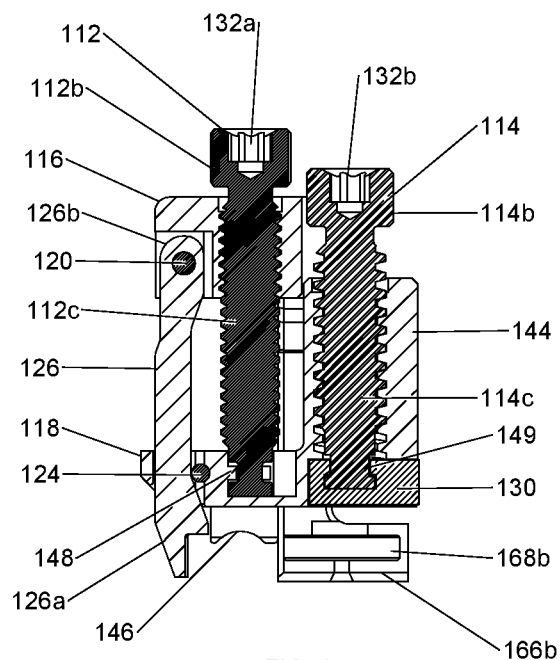
FIG. 8 is a cross-sectional view of the rod reducer of FIG. 7 cut along a section line 8-8.
Figure 14:
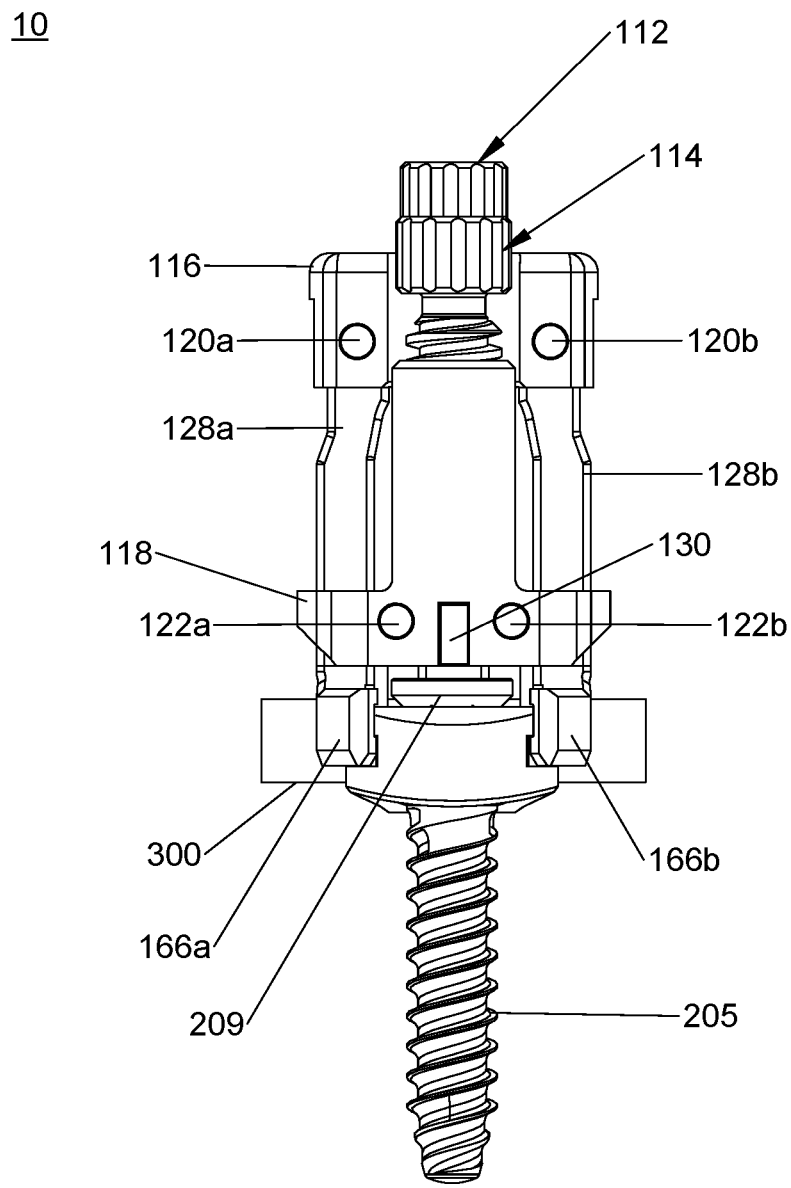
FIG. 14 is a rear view of the rod reducer and the bone screw assembly of FIG. 13.

With reference to FIGS. 4 and 8, the arm assembly 120 includes the arm 126 and first and second grasping members 128a, 128b configured to engage the bone screw housing 207 (FIG. 14). The arm 126 is dimensioned to extend through the first hole 134 (FIG. 6) of the anvil 118. The arm 126 includes a distal portion 126a and a proximal portion 126b. The proximal portion 126a is hingedly coupled to the cutout portion 158a (FIG. 5) of the housing 116 by the pin 120a. The proximal portion 126b includes the camming portion 160a, and the distal portion 126a includes a camming portion 160b having a longitudinally tapered surface. Such a configuration facilitates transition of the arm 126 between the radially contracted (closed) and radially expanded (open) positions. Each of the elongate grasping members 128a, 128b may also include respective camming portions 161a, 161b in order to facilitate radial contraction and expansion thereof. Each of the grasping members 128a, 128b includes respective lobes 166a, 166b. Each lobe 166a, 166b defines a guide channel 168a, 168b (only 168b shown) dimensioned to engage the bone screw housing 207 of the bone screw assembly 200.

With continued reference to FIGS. 4 and 8, the locking anvil 130 defines a cavity 131 dimensioned to receive the distal portion 114a of the locking screw 114. In particular, the locking anvil 130 includes a tongue portion 149 received in the annular groove 155a of the locking screw 114 to rotatably secure the locking anvil 130 with the locking screw 114, while inhibiting relative axial movement therebetween. Under such a configuration, the locking anvil 130 may be moved relative to the anvil 118. The locking anvil 130 includes a guide 130c dimensioned to be slidably received in a cutout 118c defined in the anvil 118 in order to guide axial movement of the locking anvil 130. Under such a configuration, the clinician may rotate the locking screw 114 in order to move the locking anvil 130 toward and away from the anvil 118.

Figure 10:
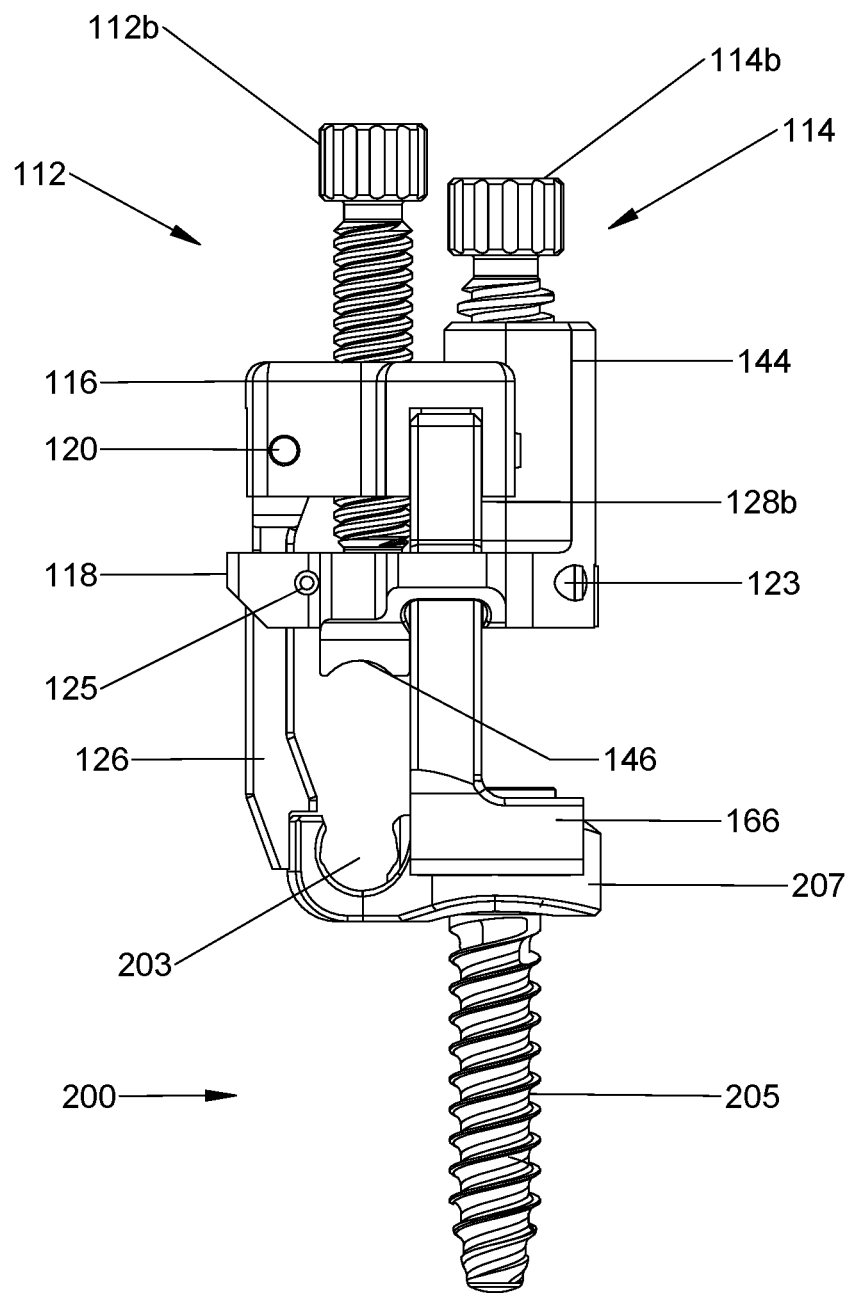
FIG. 10 is a side view of the rod reducer and the bone screw assembly of FIG. 1 illustrating the rod reducer mounted on the bone screw assembly.
Figure 11:
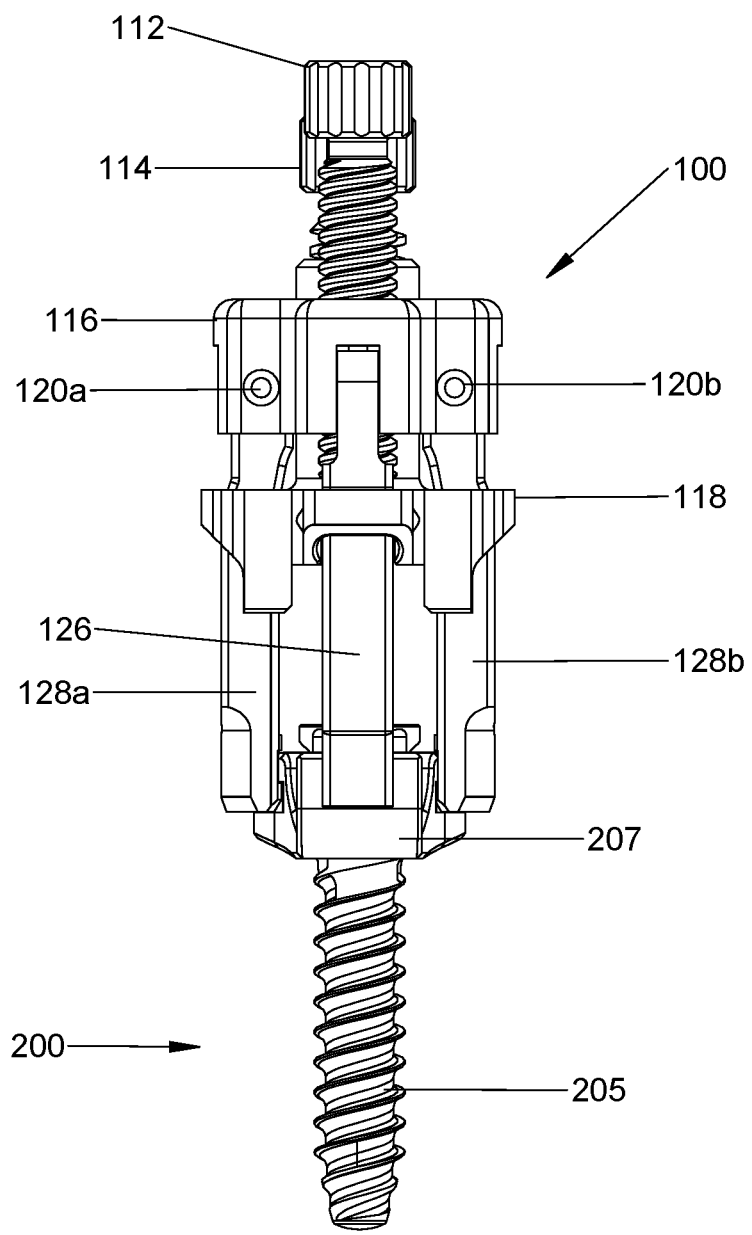
FIG. 11 is a front view of the rod reducer and the bone screw assembly of FIG. 1 illustrating the rod reducer mounted on the bone screw assembly.

With reference now to FIG. 10, the bone screw assembly 200 includes the bone screw housing 207 configured to receive a locking plug 209 (FIG. 14), a threaded shaft 205 extending distally from the bone screw housing 207, and a rod receiving portion 203 disposed adjacent the bone screw housing 207. With brief reference to FIG. 14, when the locking anvil 130 engages the locking plug 209, through rotation of the locking screw 114, the locking plug 209 is advanced into the bone screw housing 207, which, in turn, causes the rod receiving portion 203 to grasp the spinal rod 300 disposed therein, thereby securing the spinal rod 300 with the bone screw assembly 200. The locking plug 209 is movable amongst an open or unlocked state that allows insertion and/or removal of the spinal rod 300, a partially locked state that allows rotation and longitudinal movement of the spinal rod 300 relative to the bone screw assembly 200, and a locked state that securely fixes a position of the spinal rod 300 with respect to the bone screw assembly 200. This arrangement allows the clinician to reduce the spinal rod 300 into the rod receiving member 203 while still being able to perform additional adjustments to the spinal rod 300 during the procedure.

Figure 9:
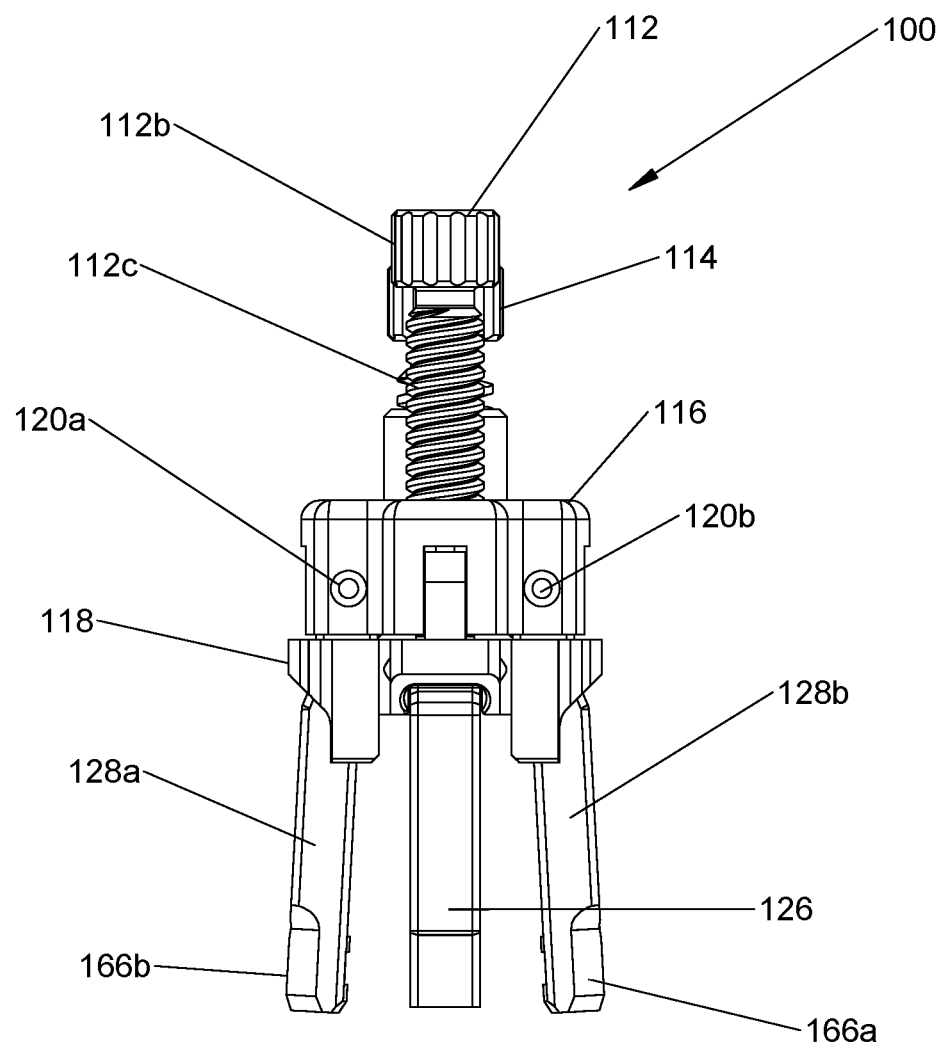
FIG. 9 is a front view of the rod reducer of FIG. 1 illustrating the reducing device in an open position.

In use, initially, the bone screw assembly 200 is mounted to a vertebra (e.g., screwed in to the vertebra) of a spine (not shown) such that the rod reducer 100 can be mounted on the bone screw assembly 200. With reference to FIG. 9, the rod reducer 100 is initially placed in an open position, in which, the arm 126 and the grasping members 128*a*, 128*b* are radially expanded by placing the reducing screw 112 in, e.g., a proximal-most position, in which the anvil 118 is positioned adjacent the housing 116. Under such a configuration, the distal portion 126*a* of the arm 126 and the lobes 166*a*, 166*b* of the grasping members 128*a*, 128*b* are spaced apart to receive the bone screw housing 207. In order to mount the rod reducer 100 to the bone screw assembly 200, the rod reducer 100 is positioned over the proximal portion of the bone screw assembly 200 (FIG. 1).

The arm 126 and the grasping members 128*a*, 128*b* are hingedly coupled to the housing 116 such that the arm 126 and the grasping members 128*a*, 128*b* can rotate radially outward about the respective pins 120*a*, 120*b*, 120*c* (FIG. 4) and transition between the radially contracted (closed) (FIG. 2) and expanded (open) (FIG. 9) positions. As the anvil 118 moves away from the housing 116, the cam pin 124 (FIG. 8) slides against the camming portion 160*a*, 160*b* (FIG. 4) of the arm 126. Similarly, as the anvil 118 moves away from the housing 116, the camming portions 161*a*, 161*b* (FIG. 4) of each of the grasping members 128*a*, 128*b* slide against the anvil 118. In this manner, the clinician can rotate the reducing screw 112 in order to move the anvil 118 distally, which, in turn, causes the arm 126 and the grasping members 128*a*, 128*b* to transition to the closed position. At this time, the lobes 166*a*, 166*b* of the grasping members 128*a*, 128*b* are secured with the bone screw housing 207, and the distal portion 126*a* of the arm 126 engages the rod receiving member 207 of the bone screw assembly 200.

At this time, the spinal rod 300 (FIG. 14) may be placed adjacent the rod receiving member 203 (FIG. 12) of the bone screw assembly 200. Alternatively, the spinal rod 300 may be placed adjacent the rod receiving member 203 prior to mounting the rod reducer 100 to the bone screw assembly 200. The clinician can further rotate the reducing screw 112 to move the rod positioning member 146 of the anvil 118 to reduce the spinal rod 300 into the rod receiving recess 203 of the bone screw assembly 200.

Figure 12:
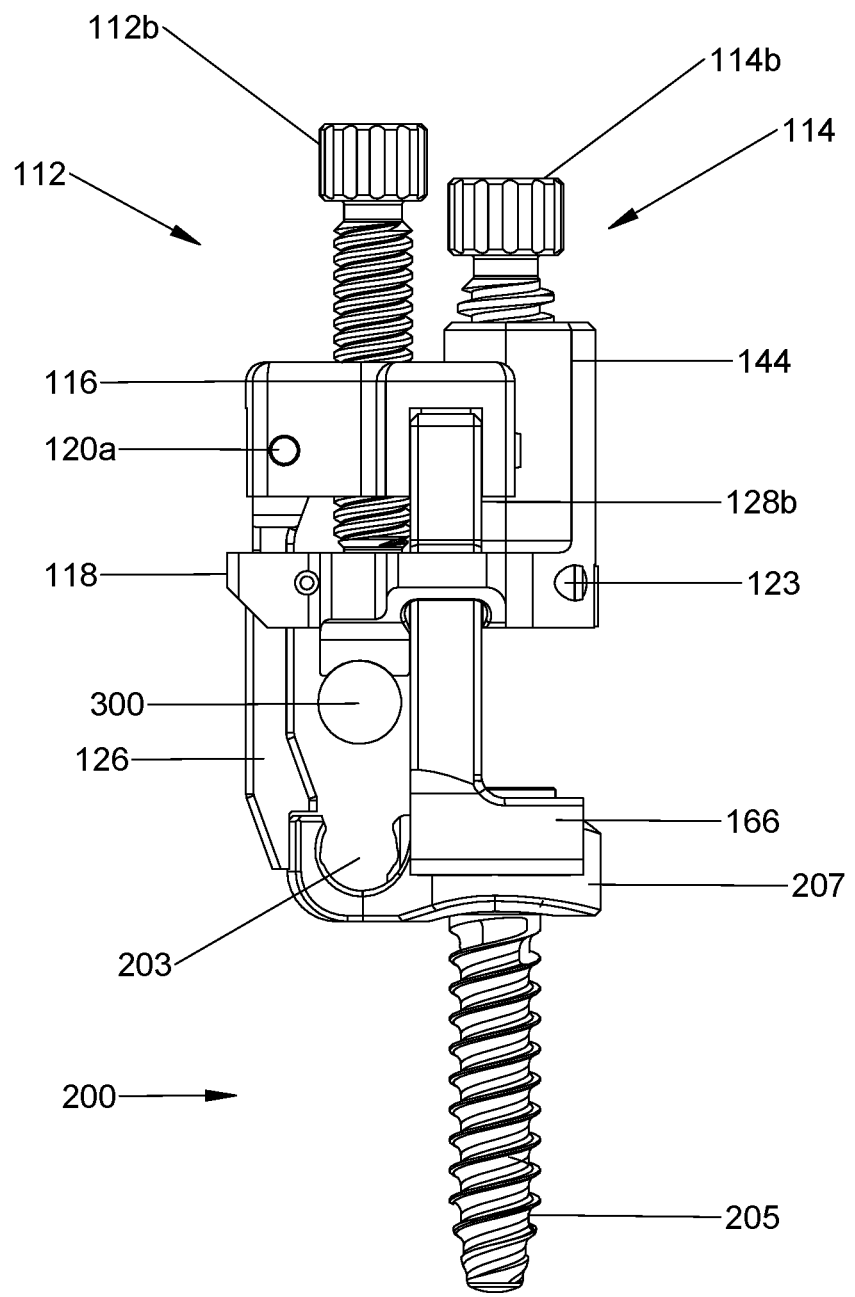
FIG. 12 is a side view of the rod reducer and the bone screw assembly of FIG. 1 illustrating use with a spinal rod.
Figure 13:
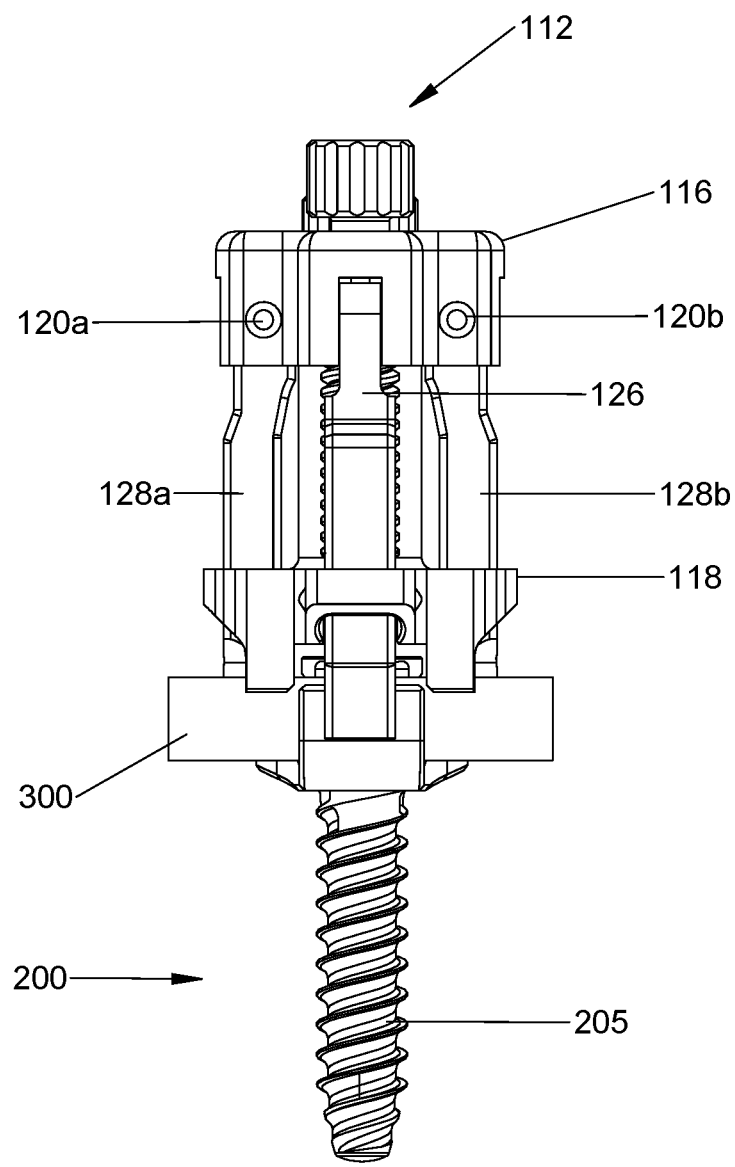
FIG. 13 is a front view of the rod reducer and the bone screw assembly of FIG. 12 illustrating reduction of the spinal rod.
Figure 15:
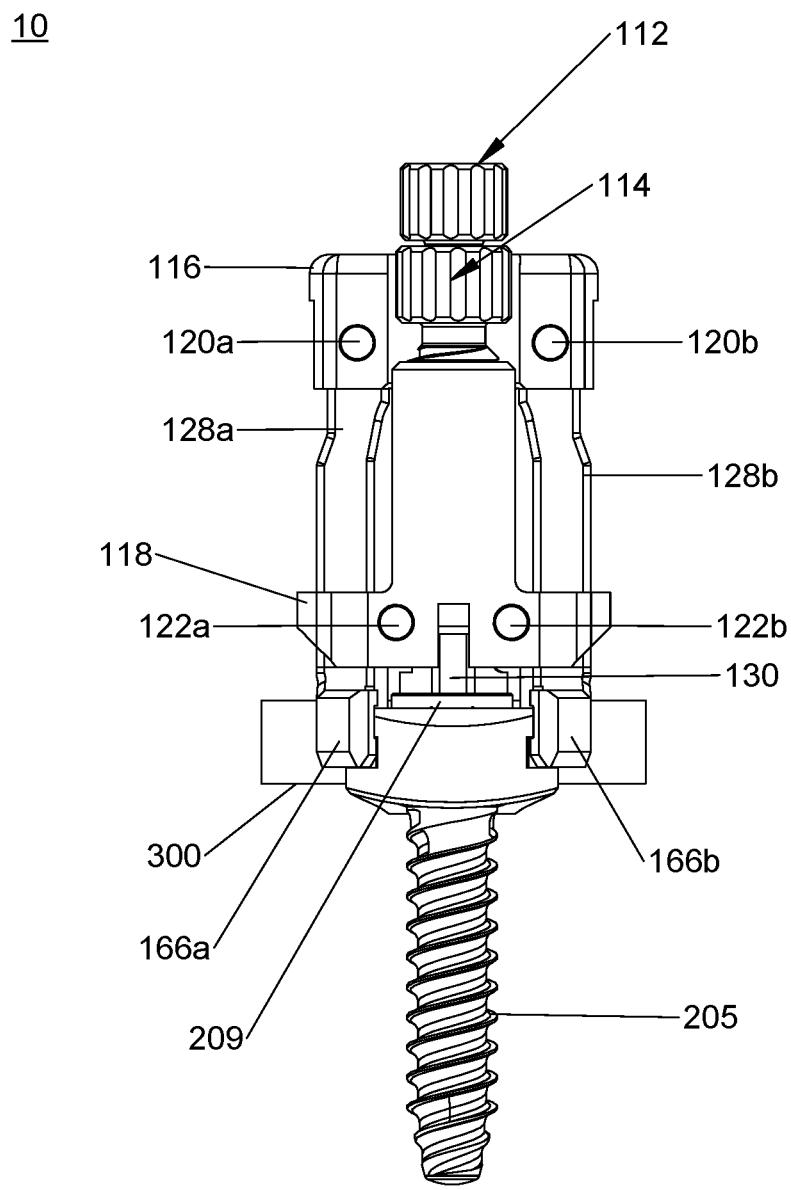
FIG. 15 is a rear view of the rod reducer and the bone screw assembly of FIG. 14 illustrating a locking anvil engaging a locking plug of the bone screw assembly.

With reference to FIGS. 12 and 14, the spinal rod 300 may be secured in the rod receiving recess 203 of the bone screw assembly 200 by utilizing the locking plug 209. In particular, the locking screw 114 may be rotated causing the locking anvil 130 to move relative to the anvil 118 toward the locking plug 209. With additional reference to FIG. 15, additional displacement of the locking anvil 130 advances the locking plug 209 into the bone screw housing 207, which, in turn, causes the spinal rod 300 to be securely fixed in the rod receiving recess 203. In this manner, the locking anvil 130 contacts the locking plug 209 and causes an interference fit which grips the spinal rod 300. It is also envisioned that the locking plug 209 may be partially locked or advanced into the bone screw housing 207 in order to make further adjustments to the spinal rod 300 as described hereinabove.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure.

Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A method of reducing a spinal rod comprising:
    transitioning a rod reducer to an open state, in which, distal ends of a first arm and grasping members of the rod reducer are radially expanded;
    positioning the rod reducer over a bone screw assembly;
    positioning a spinal rod adjacent a rod receiving portion of the bone screw assembly;
    rotating a reducing screw of the rod reducer to transition an anvil of the rod reducer away from a housing of the rod reducer to a closed state, in which, the distal ends of the first arm and the grasping members of the rod reducers are radially contracted to engage the bone screw assembly;
    reducing the spinal rod into the rod receiving portion; and
    rotating a locking screw of the rod reducer to move a locking anvil to advance a locking plug into a bone screw housing of the bone screw assembly to secure the spinal rod to the rod receiving portion, the locking screw and the locking anvil being rotatably coupled to one another.

2. The method of claim 1, wherein rotating the reducing screw of the rod reducer includes engaging the first arm of the rod reducer with the rod receiving portion of the bone screw assembly.

3. The method of claim 2, wherein rotating the reducing screw of the rod reducer includes engaging the grasping members with the bone screw housing of the bone screw assembly.

4. The method of claim 2, wherein the reducing screw is rotatably coupled with the anvil.

5. The method of claim 1, further comprising partially rotating the locking screw to partially advance the locking plug into the bone screw housing of the bone screw assembly and making adjustments to the spinal rod.

6. The method of claim 1, wherein rotation of the locking screw causes axial displacement of the locking anvil relative to the anvil.

7. The method of claim 1, wherein the locking anvil imparts an axial force to the locking plug to transition the housing of the bone screw assembly to a locked state.

8. The method of claim 1, wherein the locking anvil advances within a cutout of the anvil.

9. The method of claim 1, wherein when the locking screw is rotated, the locking screw threadably engages a threaded bore of the anvil.

10. A method of reducing a spinal rod comprising:
    positioning a rod reducer over a bone screw assembly;
    positioning a spinal rod adjacent a rod receiving portion of the bone screw assembly;
    transitioning an anvil of the rod reducer to transition a first arm and grasping members of the rod reducer from a radially expanded position to a closed position, in which, the first arm and the grasping members of the rod reducers are radially contracted to engage the bone screw assembly;

reducing the spinal rod into the rod receiving portion; and rotating a locking screw of the rod reducer to move a locking anvil to advance a locking plug into a bone screw housing of the bone screw assembly to secure the spinal rod to the rod receiving portion, the locking screw and the locking anvil being rotatably coupled to one another.

11. The method of claim 10, wherein the step of transitioning the anvil includes rotating a reducing screw of the rod reducer.

12. The method of claim 10, further comprising partially advancing the locking plug into the bone screw housing of the bone screw assembly and making adjustments to the spinal rod.

13. The method of claim 10, wherein the reducing step includes rotating a reducing screw of the rod reducer.

14. The method of claim 13, wherein the locking screw and the locking anvil are rotatably coupled together.

15. The method of claim 10, wherein rotating the reducing screw of the rod reducer includes engaging the first arm of the rod reducer with the rod receiving portion of the bone screw.

16. The method of claim 15, wherein rotating the reducing screw of the rod reducer includes engaging the grasping members with the bone screw housing of the bone screw assembly.

17. The method of claim 10, wherein the locking anvil advances within a cutout of the anvil.

18. A method of reducing a spinal rod comprising:

transitioning a rod reducer to an open state, in which, distal ends of a first arm and grasping members of the rod reducer are radially expanded;

positioning the rod reducer over a bone screw assembly;

positioning a spinal rod adjacent a rod receiving portion of the bone screw assembly;

rotating a reducing screw of the rod reducer to transition an anvil of the rod reducer away from a housing of the rod reducer to a closed state, in which, the distal ends of the first arm and the grasping members of the rod reducers are radially contracted, the grasping members engage the bone screw housing of the bone screw assembly, and the first arm of the rod reducer engages the rod receiving portion of the bone screw assembly;

reducing the spinal rod into the rod receiving portion; and rotating a locking screw of the rod reducer to axially move a locking anvil relative to the anvil to advance a locking plug into a bone screw housing of the bone screw assembly to transition the housing of the bone screw assembly to a locked state to secure the spinal rod to the rod receiving portion, the locking screw and the locking anvil being rotatably coupled to one another.

* * * * *